(12) United States Patent
Nugent et al.

(10) Patent No.: US 11,105,041 B2
(45) Date of Patent: Aug. 31, 2021

(54) METHOD OF DYEING FABRIC USING MICROORGANISMS

(71) Applicant: Colorifix Limited, Cambridge (GB)

(72) Inventors: David Glen Hastie Nugent, Cambridge (GB); Orr Yarkoni, Cambridge (GB); James Ajioka, Cambridge (GB)

(73) Assignee: Colorifix Limited, Cambridge (GB)

( * ) Notice: Subject to any disclaimer, the term of this patent is extended or adjusted under 35 U.S.C. 154(b) by 0 days.

(21) Appl. No.: 16/692,390

(22) Filed: Nov. 22, 2019

(65) Prior Publication Data

US 2020/0248403 A1  Aug. 6, 2020

Related U.S. Application Data

(63) Continuation of application No. 15/564,713, filed as application No. PCT/GB2016/000098 on May 12, 2016, now abandoned.

(30) Foreign Application Priority Data

Apr. 9, 2015 (GB) ................................ 1506018

(51) Int. Cl.
*D06P 1/34* (2006.01)
*C12P 1/04* (2006.01)
*C12P 17/16* (2006.01)

(52) U.S. Cl.
CPC ................ *D06P 1/34* (2013.01); *C12P 1/04* (2013.01); *C12P 17/165* (2013.01)

(58) Field of Classification Search
CPC .............. D06P 1/34; C12P 1/04; C12P 17/165
See application file for complete search history.

(56) References Cited

U.S. PATENT DOCUMENTS

| | | | |
|---|---|---|---|
| 2,297,230 A | 9/1942 | Langen | |
| 3,846,141 A | 11/1974 | Ostergren et al. | |
| 4,520,103 A | 5/1985 | Ensley, Jr. | |
| 4,752,301 A * | 6/1988 | Koch | C09B 7/02 |
| | | | 435/118 |
| 5,077,201 A | 12/1991 | Eyal et al. | |
| 5,112,747 A | 5/1992 | Van Grinsven et al. | |
| 5,691,171 A | 11/1997 | Oriel et al. | |
| 5,834,297 A | 11/1998 | Oriel et al. | |
| 5,872,002 A | 2/1999 | Sugiura et al. | |
| 6,436,696 B1 | 8/2002 | Hsieh et al. | |
| 2011/0183384 A1 * | 7/2011 | Xing | C12N 15/52 |
| | | | 435/118 |

FOREIGN PATENT DOCUMENTS

| | | | | |
|---|---|---|---|---|
| CN | 102634993 | * | 8/2012 | ............ D06M 15/03 |
| EP | 0 252 002 | | 1/1988 | |
| JP | 55019070 | | 2/1980 | |
| JP | 55148091 | | 11/1980 | |
| JP | 07227290 | | 2/1994 | |
| JP | 06253864 | | 9/1994 | |
| JP | 06257074 | | 9/1994 | |
| JP | 06284893 | | 10/1994 | |
| JP | 06341069 | | 12/1994 | |
| JP | 0734387 | | 2/1995 | |
| JP | 10113169 | | 5/1998 | |
| JP | 2810287 | | 7/1998 | |
| JP | 63245666 | | 10/1998 | |
| JP | 06253864 | | 9/2013 | |
| JP | H06253864 | * | 9/2013 | ............... C12P 1/00 |
| JP | 2016-036285 | | 3/2016 | |
| KR | 2006120867 | | 11/2006 | |
| WO | 2006/019672 | | 2/2006 | |
| WO | WO2011110932 | * | 9/2011 | .............. C12P 17/06 |
| WO | 2016/162657 | | 10/2016 | |

OTHER PUBLICATIONS

Park, Derwent 2007-7156475, 2007.*
Aoki, Derwent 1995-331527, 1999.*
Jiang, Derwent 2013-A78865, 2014.*
LB (Luria-Bertani) liquid medium; http://cshprotocols.cshlp.org/content/2006/1/pdb.rec8141.full?text_only=true, Aug. 16, 2020.*
Ohtani, T. et al., "Factors for filament formation of gluconobacter cerinus", Gluconobacter Cerinus, vol. 42, pp. 81-91, (1985).
Chequer, F.M.D. et al., "Eco-friendly textile dyeing and finishing: Textile Dyes: Dyeing process and environmental impact", Intech Open Science, chapter 6, pp. 151-176, (2013).
Hart, S. et al., "Identification of indigo-related pigments produced by *Escherichia coli* containing a cloned *Rhodococcus* gene", Journal of General Microbiology, vol. 138, pp. 211-216 (1992).
Tao, J-I. et al., "Strategy for the improvement of prodigiosin production by a *Serratia marcescens* mutant through fed-batch fermentation", World Journal of Microbiology & Biotechnology, vol. 21, issue 6-7, pp. 969-972, (2005).
Rettori, D. et al., "Production, extraction and purification of violacein: an antibiotic pigment produced by *Chromobacterium violaceum*", World Journal of Microbiology & Biotechnology, vol. 14, issue 5, pp. 685-688, (1998).

(Continued)

*Primary Examiner* — Amina S Khan (74) *Attorney, Agent, or Firm* — Evan Law Group LLC (57) ABSTRACT

This invention relates to a method for dyeing fabrics, yarns and fibers using microorganisms whereby the adsorption of dye-containing microorganisms onto textile fibers is improved using carbon sources above a threshold concentration. Dye molecules contained within the microorganism are released from the microorganism and fixed directly and locally to the textile fibers using a heat treatment step. Said heat treatment also deactivates the carrier microorganisms. Single or multiple microorganism species, and single or multiple dyes produced by said single or multiple microorganism species may create a variety of textile colors. Suitable synthetic dyes may also be added before, during or after microorganisms have produced dyes but before the dye-releasing heat treatment step.

30 Claims, 10 Drawing Sheets

(56) References Cited

OTHER PUBLICATIONS

"Uses of glycerine", The Glycerine Producers' Association, pp. 1-29, (1963).
Technicus, "Printing of Rayons", Rayon Textile Monthly, vol. 24, p. 65, (1943).
Leffingwell, G., "Textile applications for glycerine", Textile Research Journal, vol. 14, No. 3, pp. 69-73, (1944).
Bennett, H., "The Chemical Formulary: A collection of valuable, timely, practical commercial formulae and recipes for making thousands of products in many fields of industry", vol. VI, Chemical Publishing Company, pp. 518-519, (1943).
Photo Marketing Association International, "Digital imaging: water-based inks and HSE", fact sheet 3, pp. 1-2, (2004).
Da Silva, G.P. et al., "Glycerol: A promising and abundant carbon source for industrial microbiology", Biotechnology Advances, vol. 27, pp. 30-39, (2009).
Saegeman, V.S.M., et al., "Short- and long-term bacterial inhibiting effect of high concentrations of glycerol used in the preservation of skin allografts", Burns, vol. 34, issue 2, pp. 205-211, (2008).
Feng, Y. et al., "Effects of glycerol on pigments and monacolin K production by the high-monacolin K-producing but citrinin-free strain, *Monascus pilosus* MS-1", European Food Research and Technology, vol. 240, pp. 635-643, (2014).
Venil, C.K. et al., "Bacterial pigments and their applications", Process Biochemistry, vol. 48, pp. 1065-1079, (2013).
International Search Report and Written Opinion dated Sep. 22, 2016 for PCT application Serial No. PCT/GB2016/000098.
China Application No. 201680020663.7, dated Feb. 2, 2021, 13 Pages.
China Application No. 201680020663.7, dated Jul. 8, 2020, 12 Pages.
EP Application No.16723798.1, dated Feb. 22, 2019, 32 Pages.
EP Application No. 16723798.1, dated Jul. 24, 2018, 7 Pages.
GB Application No. GB1506018.9, dated Sep. 2, 2019, 2 Pages.
GB Application No. GB1506018.9, dated Dec. 3, 2018, 4 Pages.
GB Application No. GB1506018.9, dated Dec. 12, 2017, 4 Pages.
GB Application No. GB1506018.9, dated Dec. 23, 2015, 7 Pages.
GB Application No. GB1506018.9, dated Jun. 25, 2019, 3 Pages.
Japan Application No. 2018-503829, dated Dec. 22, 2020, 2 Pages.
Viet Nam Application No. 1-2017-03989, dated Nov. 30, 2020, 3 Pages.
Thailand Application No. 1701006052, dated Oct. 25, 2019, 7 Pages.
Thailand Application No. 1701006052, dated Jul. 28, 2020, 4 Pages.
Jjemba, P.K. et al., "In-situ enumeration and probing of pyrene-degrading soil bacteria", FEMS Microbiology Ecology, vol. 55, pp. 287-298, (2006).

\* cited by examiner

METHOD OF DYEING FABRIC USING MICROORGANISMS

This invention relates to a method for dyeing fabrics, yarns and fibers using microorganisms whereby the adsorption of dye-containing microorganisms onto textile fibers is improved using carbon sources above a threshold concentration. Dye molecules contained within the microorganism are released from the microorganism and fixed directly and locally to the textile fibers using a heat treatment step. Said heat treatment also deactivates the carrier microorganisms. Single or multiple microorganism species, and single or multiple dyes produced by said single or multiple microorganism species may create a variety of textile colors. Suitable synthetic dyes may also be added before, during or after microorganisms have produced dyes but before the dye-releasing heat treatment step.

Dye Production

Most contemporary fabric dyes are synthesized chemically and require toxic precursors and solvents. It is estimated that over 10,000 different dyes and pigments are used industrially with over 700,000 tonnes of synthetic dye being produced annually worldwide (Chequer et al., 2013, Eco-friendly textile dyeing and finishing, pp. 151-176).

Microbial production of pigments has been studied for hundreds of years. For pigments such as prodigiosin and violacein, naturally occurring microbes have been specifically cultured for pigment production (JP10113169; JP55019070A; JP55148091; JP63245666A).

U.S. Pat. No. 4,520,103 to Ensley describes a method for production of indigo with a recombinant bacterium in a medium that is indole free. Use of specific strains of a recombinant *E. coli* to produce indigo or indigotin from indole is particularly described using a gene encoding an aromatic dioxygenase from another bacterium to convert the indole.

Indole preparation is described in U.S. Pat. No. 5,112,747 to Van Grinsven et al. Hart et al (Microbiology 138 211-216 (1992) described a recombinant *E. coli* containing a cloned *Rhodococcus* gene for producing indigo and indirubin. Indole is produced which is oxidized to indigo.

U.S. Pat. No. 5,077,201 to Eyal et al describes a novel mutant strain of Morel mushroom which has been found to produce the blue pigment indigo by submerged fermentation in a nutrient culture medium containing a carbon and a nitrogen substrate.

Numerous carbon sources have been evaluated for the microorganism pigmentation including glycerol, maltose, sucrose, citrate, lactose and glucose (World Journal of Microbiology & Biotechnology (2005) 21: 969-972). As discussed elsewhere in this document, carbon sources such as glycerol act as antibacterial agents at concentrations exceeding 10% (v/v). Correspondingly these compounds are used as carbon sources during microorganism pigment production at mild concentration typically <5% (v/v), more commonly 1% (v/v).

Dye Extraction

Once pigments that work as dyes have been produced by the microbe, extraction procedures include the use of organic solvents such as chloroform, ether, ethyl acetate, aqueous sulfuric acid, acetone, hexane, benzene, ethanol or methanol (U.S. Pat. Nos. 5,077,201; 5,691,171; Rettori and Duran, 1998, *World J. Microbiol. Biotech* 14: 685-688; JP10113169; JP63245666 A), or boiling the microbe in an aqueous solution (JP2810287B2; JP10113169). Solvent extraction produces waste chemicals that are difficult and expensive to recycle or dispose of and are highly deleterious to aquatic life if discharged into waterways.

Secondary pigment extraction steps may include volume reduction, solvent change, or sonication or freezing (U.S. Pat. Nos. 5,834,297; 5,691,171).

Fabric Pre-Treatment

U.S. Pat. No. 6,436,696 discloses the treatment of textile fibers with enzymes in the absence of surfactants, with the effect of increasing the wettability and absorbency of the fibers. The enzymes are pectinases, cellulases, proteases, lipases or combinations thereof. The wetting properties of cotton fibers are found to be most substantially improved by treatment with a mixture of cellulase and pectinase. As disclosed in U.S. Pat. No. 6,436,696, said enzymes can be produced by microorganisms including fungi and bacteria. Microorganisms that produce suitable lipases include *Candida ancudensis, Candida Antarctica, Candida atmaspherica, Candida bombi, Bacillus amyloliquefaciens, Bacillus megaterium, Bacillus subtilis* and many others.

Known fabric pre-treatments have been used in the dyeing process for microbially produced dyes. Pre-treatments include: 1) standard soap, anhydrous sodium carbonate, L-histidine mono-hydrochloride mono-hydrate, NaCl and NaHPO4 for fabric swelling and removal of impurities and 2) mordants such as alum, copper sulfate, ferrous sulfate, sodium silicate, slaked lime and tamarind preparation (Chequer et al., 2013, Eco-friendly textile dyeing and finishing, pp. 151-176).

Dye Deposition

Since the 1940s both glycerol and glycerol-derived alkyds have found widespread application in many dyeing and printing procedures for textiles (Uses of Glycerol, compiled by The Glycerol Producers' Association). Glycerol itself produces dyestuff pastes of excellent workability, promotes the fixation of dyes in printing pastes, increases color value in printing and assists in the retention of moisture in the ager.

Glycerol is an ingredient of many dyes shipped in paste form since it prevents the dyes from drying out, and sticking to the sides of the drum. Its non-corrosiveness and low freezing point are desirable in this application. During dyeing, the water miscibility of the glycerol present in the dye paste and its solvent action on many types of dyestuffs aid in dispersing the latter in the dye bath, where the high boiling point of glycerol is another advantage. Occasionally glycerol is added directly to the dye bath as was the case with the nylon dyeing formulas developed by the Nylon Task Committee during World War II to meet the washfastness and other requirements of the Quartermaster Corps. In naphthol dyeing, glycerol is sometimes used before coupling to improve stability of the naphthol solution.

The concentration of glycerol typically used in dye mixtures and dye pastes is limited to minimize the time required to dry fabrics post-dyeing and reduce marking off difficulties respectively ("Techniques" Rayon Textile Mo. 24, 65, August 1943). In one case, to dye blue shades, the following mixture was used: 1.7 kg Chlorindanthrene Blue; 39.0 litres Sodium Hydroxide; 6.4 kg hyposulfate; and 0.5 kg glycerol (Textile Research Journal March 1944 vol. 14 no. 3 69-73). Here the glycerol concentration was 1.1% (v/v).

According to Bennett, H., "Chemical Formulary," Vol. VI, New York, Chem. Publishing Co., pp. 518-9, 1943, a typical textile printing dye contains: 20 grams direct color; 310 grams hot water; 50 grams glycerol; 20 grams sodium phosphate; 500 grams starch-based thickeners; 100 grams egg albumin. Contemporary acid print pastes prescribed online by Robert Gordon University contain 0.1-3 grams acid dyestuff, 5 grams glycerol; 20 mls warm water; 60 grams Manutex RS; 2 grams Ammonium Oxalate; and 5 mls of hot water. Thus it can be observed that the recommended concentration of glycerol contained in fabric printing dyes has remained at 5% (v/v) for over 70 years.

Other dyeing procedures in which glycerol finds application include the vat dyeing of acetate fabrics, the dyeing of cottons with direct colors, and the preparation of dyeing compounds for use on wool, silk, cotton, synthetic fibers and particularly rayon and staple fibers made from cellulose. Spray dyeing processes frequently utilize glycerol as a solvent, dispersant and suspending agent for dyes or pigments. The nonfoaming characteristics of the resulting compositions promote even dyeing. It may also be used to produce blended tints of "umbray" effects. Besides this, it has application in fluid bed dyeing, dispersed acetate dyes and azoic dyes.

Glycerol has also been used as a textile-conditioning agent used widely in the lubrication, sizing, and softening of yarn or fabric. Its effectiveness in these and similar applications is due mainly to viscosity and hygroscopicity, both properties contributing to the plasticizing action. Hygroscopic, or humectant, qualities also account for the utilization of glycerol in special treatments, such as processes to increase the wearability of fabrics or to prevent static charges on fibers. Because of impermeability to poison gas, particularly "mustard", glycerol has found application in gas-resistant finishes. Water solubility is an asset too when glycerol serves as a lubricant. This obviates the need for strong scouring agents, which tend to injure the fabric but which must often be used to remove other lubricating oils.

As an additive to lubricating compositions, sizes, or various finishes, glycerol acts as a plasticizer, solvent, and penetrant. It prevents drying out and caking on the fiber, eliminates the dusting of sizes, and may aid in dispersing water-insoluble lubricating oils applied from a water bath.

Glycerol is also included in aqueous and solvent-based print ink formulations. Here this substance acts as a humectant to inhibit evaporation of the carrier fluid whilst controlling ink viscosity and thereby fluid dynamics during the deposition process. Ink deposition processes may include inkjet printing, screen printing, pad printing etc. Typically the concentration of glycerol plus other humectants in the ink formulation is <20% (v/v) (Digital Imaging: Water-based Inks and HSE, Photo Marketing Association International, 2004). As explained in U.S. Pat. No. 3,846,141 Jet printing ink composition, higher concentrations of glycerol or other humectants cannot be used in jet printing because the ink compound becomes too viscous and consequently its passage through the jets becomes inhibited.

WIPO Patent Application WO/2006/019672 describes the inclusion of glycerol in an eradicable ink formulation. Here glycerol is present in an amount greater than the water content, which is relatively low, and the eradicable dye is provided in substantial amounts so that the glycerol and eradicable dye provide the requisite viscosity for a ball-pen ink. Here water is present in an amount ranging from about 10 to about 20% (v/v) and the glycerol is present in an amount ranging from about 30 to about 50% (v/v).

In all of the aforementioned circumstances glycerol is used to change the physical properties, primarily viscosity and hygroscopy, of the aqueous or solvent-based carrier fluid but not on the colorant itself such as azo dye or pigment. More specifically, glycerol has no meaningful, purposeful or intentional interactions with the colorant directly regardless of the presence or absence of a carrier fluid.

U.S. Pat. No. 5,872,002 describes a method of textile patterning using microorganisms to decolorize fabrics previously dyed with an azo dye (which may also contain a non-azo dye). This technique is based on the ability of bacterial strains such as *Xanthomonas* NR25-2 to metabolize azo dyes comprising a variety of isomers. Using either patterned heating elements, or patterned acidic pastes, or patterned alkaline pastes, or patterned disinfectants, regions of bacterial strains deposited onto a fabric are deactivated thereby preserving the azo colouring. Notably these bacterial strains do not produce or deposit pigments themselves but remove azo dyes by partially or completely metabolizing a previously deposited azo dye.

Extracted microbially produced dyes in solution can be deposited directly onto the fabric with a conventional procedure (JP10113169; JP2810287B2). For violacein and prodigiosin, this has been shown to work on a variety of fabric types (Yusof et al., 2012, *Application of bacterial pigments as colorant: the Malaysian perspective*).

Glycerol is widely reported as a carbon source for microbe production (Biotechnology Advances 27 (2009) 30-39). Typically the concentration of glycerol in M9 media is 2% (v/v). Higher concentrations of glycerol tend to inhibit microbial growth. Indeed glycerol has been studied as an antibacterial agent for the long-term preservation of skin allografts (Burns, Volume 34, Issue 2, 205-211).

Dye Fixation

For extracted microbially produced dyes, mordanting (see Fabric pre-treatment) has been shown to improve dye transfer, yielding darker coloured fabric (Chequer et al., 2013, *Ecofriendly textile dyeing and finishing*, pp. 151-176; Yusof et al., 2012, *Application of bacterial pigments as colorant: the Malaysian perspective*). Some methods include the addition of post-dyeing mordants such as metal salts. Heat treatment for dye fixation is commonly used, with methods including heating in solution at temperatures above 80° C. (JP10113169; Chequer et al., 2013, *Eco-friendly textile dyeing and finishing*, pp. 151-176).

U.S. Pat. No. 2,297,230 describes the use of glycerol as an additive during a textile steam treatment process. Here glycerol serves to strengthen the binding of Turkey Red oil, a synthetic detergent, into the fabric during a steam treatment. U.S. Pat. No. 2,297,230 further specifies that glycerol should be dispensed in conjunction with formalin (formaldehyde in water) to prevent to a considerable extent the formation of mildew and spores. Hence U.S. Pat. No. 2,297,230 is not relevant to this Invention because: (a) it does not relate to textile dyeing, (b) employs steam and not liquid water, and (c) includes a substance that would be highly deleterious to the microbiological process specified in this Invention.

Waste Management

All the above steps require waste management and water economy as many dyes, their precursors and the solvents used to produce and extract them are hazardous to human health and the environment. The textile industry consumes a substantial amount of water in its manufacturing processes, mainly due to the dyeing process. Waste water from textile plants is classified as the most polluting of all industrial processes (Chequer et al., 2013, Eco-friendly textile dyeing and finishing, pp. 151-176).

In the dyeing process, 10-50% of the dye is lost as waste and ends up in the effluent (Chequer et al., 2013, Eco-friendly textile dyeing and finishing, pp. 151-176). On a global scale, this results in $2 \times 10^5$ tonnes of dye being released into the environment annually (Chequer et al., 2013, Eco-friendly textile dyeing and finishing, pp. 151-176). On average, the ratio of the required water-to-fabric mass is up to 100:1 (Huntsman Textile Effects, Singapore).

In conclusion, existing methods for producing fabric dyes and transferring and fixing said dyes to fabrics, yarns and textiles necessitates the production and usage of toxic chemicals and the generation of toxic wastes. Furthermore the consumption of water during dyeing processes and subsequent wastewater treatment impose significant burdens on local water demand. Whilst the merits of glycerol as a dye additive and fabric treatment agent are widely acknowledged, concentrations of this substance are limited to low levels (typically less than 5% (v/v)). Whilst microbiological production of fabric dyes has been discussed, such methods do not extend to improved methods for extracting, depositing and fixing said dyes into the fabric yarns.

SUMMARY OF INVENTION

This process can be achieved by observing the conditions below when dyeing substrates (such as fabrics) directly using microorganisms that act as agents for substrate pre-treatment as well dye production, deposition and fixation.

For dye production, both natural (non-recombinant) microorganisms capable of producing both intermediate and end point pigments as well as recombinant microorganisms which have been modified so as to be able to produce either intermediate or end point pigments can be used in this process.

Pre-treatment (including substrate modification of any type) occurs via the action of metabolic processes conducted by microorganisms permeating the substrate and by the medium compositions which facilitate these processes. Pre-treatment allows for more effective dye penetration/permeation/fixation in the substrate. Dye deposition is achieved via localized production and release of the dye by the microorganism which have permeated the substrate. Increased local concentrations lead to higher dye uptake and the substantial reduction of large amounts of free dye in solution lead to a substantially reduced amount of waste product. In the dye fixation step, the vast majority of dye present in the inactivated microorganism is transferred to the substrate due to lysis.

Dye fixation is achieved via exposure of the treated substrate to temperatures exceeding 121° C. This has the dual purpose of inactivating all microorganisms present on the substrate as well as fixation of the dye to the substrate. Industrial automatic autoclaves machine, made by Sparrow Tex Engineering Works and Bluemoon Machines Manufacturing Company, can be used for heat setting and conditioning of yarn in various capacity ranges.

A final wash step removes the vast majority of inactivated microorganisms and microorganism related detritus from the substrate. The final substrate has then been sterilized and cleaned to a standard nearing medical device requirements.

Advantageously the described methods surpass conventional methods of dye production, dye transfer and dye fixation in regards to waste generation, water consumption, and energy consumption. Wastes generated using the described process do not include any of the following: organic solvents, concentrated acidic or alkali products, such as bleach. Handling, inactivation and disposal of the waste products deriving from this process becomes safe and inexpensive in comparison to conventional methods. All waste products generated from this process are biodegradable compounds. Some of the waste products generated from this process may have commercial value, for example as a plant fertilizer.

BRIEF DESCRIPTION OF THE DRAWINGS

The invention can be better understood with reference to the following drawings and description.

DETAILED DESCRIPTION OF THE EMBODIMENTS

The features and advantages of the present invention will be more readily understood, by those of ordinary skill in the art, from reading the following detailed description. It is to be appreciated those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. Also, the disclosure of these ranges is intended as a continuous range including every value between the minimum and maximum values.

All patents, patent applications and publications referred to herein are incorporated by reference in their entirety.

This process aims to combine substrate pre-treatment and localized production, deposition and fixation of substrates (such as fabrics). Fabrics can be natural (cotton, silk, wool and others of a similar nature) or synthetic (polyester, rayon, elastaine and others of a similar nature) in composition.

Dye production is achieved via use of a microorganism capable of producing pigments with properties desired in a dye. Both natural (non-recombinant) microorganisms capable of producing both intermediate and end point pigments and recombinant microorganisms which have been modified so as to be able to produce either intermediate or end point pigments can be used in this process. Examples include but are not limited to: *Serratia* spp, *Janthinobacter* spp., *Chromobacterium* spp., *Bacillus* spp., *Escherichia* spp., *Cyanobacterium* spp., *Pseudomonas* spp. As an example, a K12 derivative of *E. coli* has been modified to produce high quantities of violacein by introducing a plasmid that carries a re-factored violacein operon. The re-factoring includes a re-arrangement of the order of enzyme coding sequences, the addition of ribosome binding sites in front of each coding sequence and codon optimisation of the coding sequences for expression in *E. coli*.

Virtually any microorganism which can be genetically modified may be incorporated into this process. The innovative step regarding this process is in the direct application of the microorganism to the substrate in order to facilitate localized dyeing of the substrate.

Pre-treatment (including substrate modification of any type) occurs via the action of metabolic processes conducted by microorganisms permeating the substrate and by the medium compositions which facilitate these processes. Pre-treatment allows for more effective dye penetration, permeation and fixation in the substrate.

The pre-treatment step is performed by the microorganism in a wide range of conditions which drive microorganism metabolism via various parameters, such as nutrient content, pH and salinity. The nature of the microorganism employed in this process will dictate the optimum composition of the medium. As an example, *Chromobacterium violaceum* requires a very different optimal environment than *Escherichia coli*.

As an example of embodiment of this invention, a K12 derivative of *E. coli* which has been modified to produce high quantities of violacein was used to pre-treat the following substrates: silk, wool, rayon, polyester, elastaine, cotton and flax. The medium compositions used to pre-treat the substrate with the above mentioned strain of *E. coli* include the following base components: carbon source, nitrogen source, amino acid source, metal salt source and water.

Explanation

Without wishing to be constrained by theory, we believe the improved adsorption of dye-containing microorganisms into the textile fabric is caused by changes in the morphology of these microorganisms when exposed to a carbon source when this carbon source is beyond a threshold concentration. More specifically, beyond a certain concentration of carbon source the microorganisms become significantly longer and distorted in shape. Longer microorganisms are more likely to become entangled in the fabric yarns whilst contortions along their length means they are harder to be dislodged from their anchoring amongst the fibers. The precise concentration threshold will depend on numerous factors such as the microorganism species, the carbon source used, and operating conditions such as temperature and pH level. Generally speaking we have found the threshold concentration is in the range 10% (v/v) to 60% (v/v), more commonly 20% (v/v) to 40% (v/v).

FIGURES

FIG. 1 shows a method for growing and depositing pigments produced by microorganisms according to JP2810287B2. FIG. 1A shows a first step where a single pigment-producing bacteria species (1) is inoculated in a media solution (2). FIG. 1B shows a second step where the bacteria are inoculated in a second media solution (3) for 18 hours at 30° C. FIG. 1C shows a third step where a wool decomposition product (4) is added to the media solution and shaken for five days at 30° C. FIG. 1D shows a fourth step where threads (5) are added to the media solution whilst some of the pigments contained within the microorganisms are released into the media solution (6) by boiling the media solution at 100° C. for 20 minutes. FIG. 1E shows a sixth step where the threads are removed from the dye bath after boiling and washed under running water to remove residual media solution and loose pigments. An unspecified quantity of pigments shall remain in the media solution (7) and attached to the wool decomposition product (8).

FIG. 2 shows the method for dyeing textiles according to this invention. Before the first dyeing step, dye-producing microorganisms (10) are prepared according to standard microbiology methods. These methods may include techniques such as synthetic biology and genetic engineering. A single colony of the microorganism is inoculated in media solution according to standard methods.

Figure 1A:
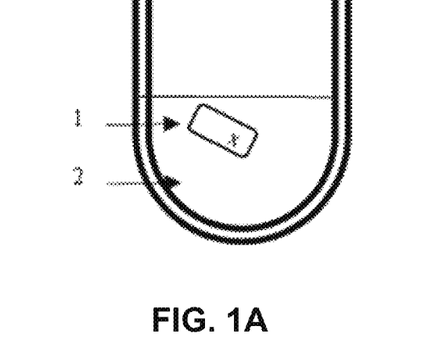
FIG. 1A illustrates the first step of the method for growing and depositing pigments produced by microorganisms according to JP2810287B2 showing a pigment-producing bacteria species inoculated in a media solution.
Figure 1B:
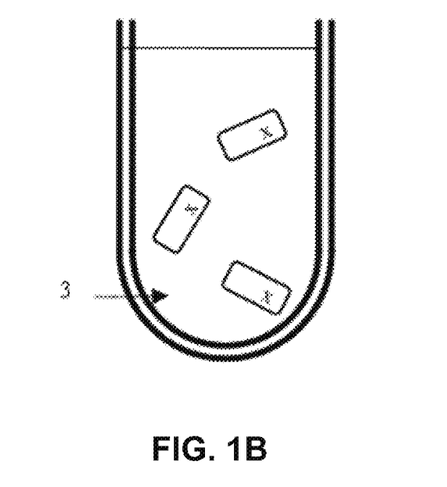
FIG. 1B illustrates the second step of the method for growing and depositing pigments produced by microorganisms according to JP2810287B2 showing bacteria inoculated in a second media solution.
Figure 1C:
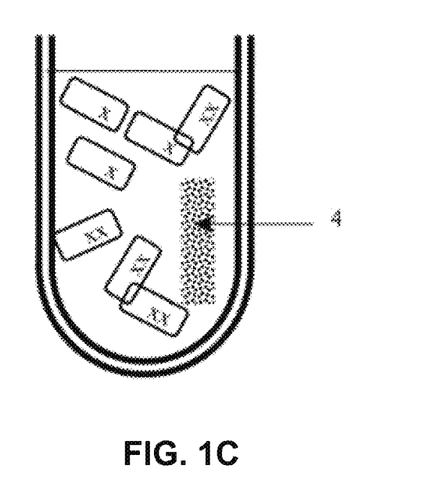
FIG. 1C illustrates the third step of the method for growing and depositing pigments produced by microorganisms according to JP2810287B2 showing a wool decomposition product added to the media solution.
Figure 1D:
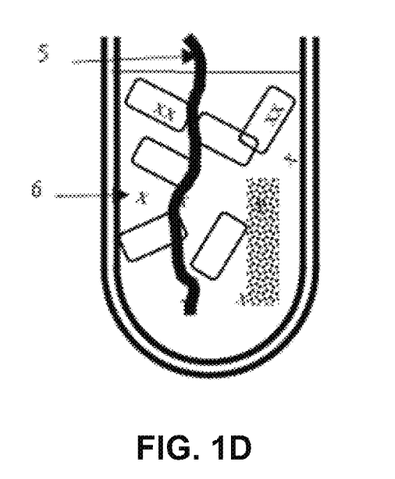
FIG. 1D illustrates the fourth step of the method for growing and depositing pigments produced by microorganisms according to JP2810287B2 showing threads added to the media solution and some of the pigments contained within the microorganisms released into the media solution.
Figure 1E:
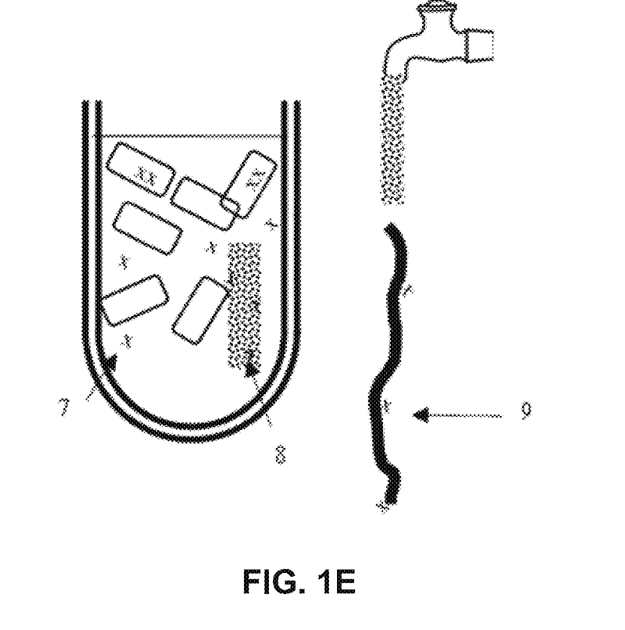
FIG. 1E illustrates the fifth step of the method for growing and depositing pigments produced by microorganisms according to JP2810287B2 showing threads removed from the dye bath and washed under running water.
Figure 2A:
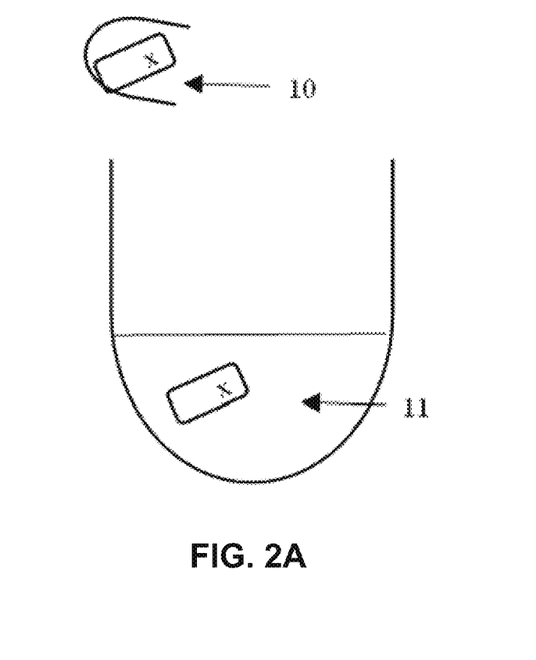
FIG. 2A illustrates a method for dyeing textiles according to the present invention showing a dye-producing microorganism inoculated in a volume of media solution.
Figure 2B:
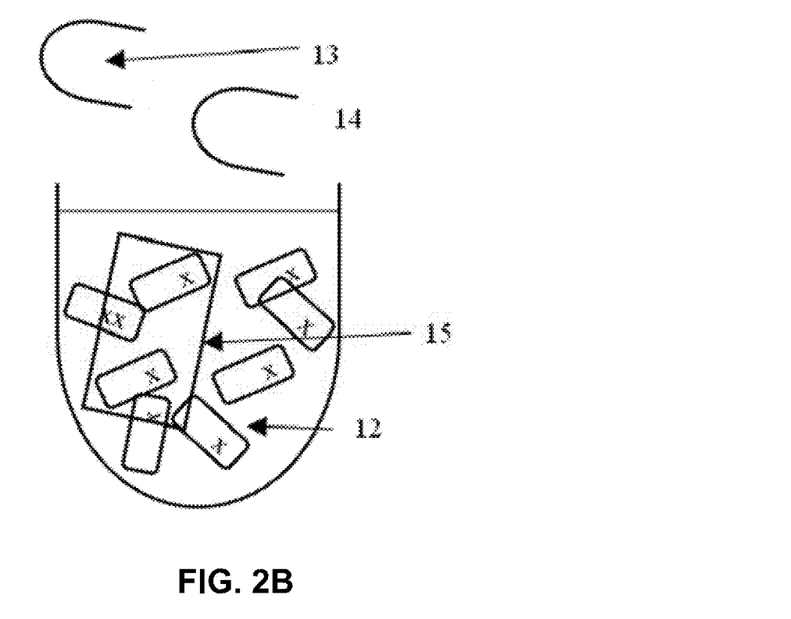
FIG. 2B illustrates a method for dyeing textiles according to the present invention showing a culture medium containing dye-containing microorganisms, a volume of media solution, a second volume of carbon source and a substrate.

In a first dyeing step, the dye-producing microorganism (10) is inoculated in a volume of media solution (11) and allowed to grow overnight according to standard microbiology techniques. The resulting culture medium containing high concentrations of dye-containing microorganisms (12) is then supplemented with a volume of media solution (13)

and a second volume of carbon source (14). The resulting concentration of carbon source should be in the range 10% (v/v) to 90% (v/v), preferably 15% (v/v) to 60% (v/v), more preferably 20% (v/v) to 40% (v/v). A substrate (15), i.e. fabric or yarn, is added to the culture and incubated overnight according to standard methods.

Figure 2C:
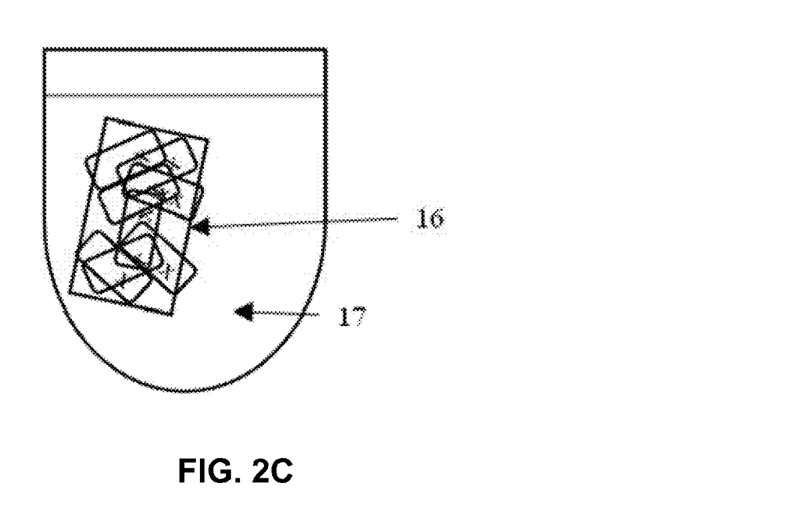
FIG. 2C illustrates a method for dyeing textiles according to the present invention showing dye-containing microorganisms adsorbed into a substrate.

After overnight incubation the vast majority of dye-containing microorganisms will be adsorbed into the substrate (16) including the spaces between neighboring fibers. Correspondingly the culture media and carbon source solution (17) shall be substantially bereft of microorganisms.

Figure 2D:
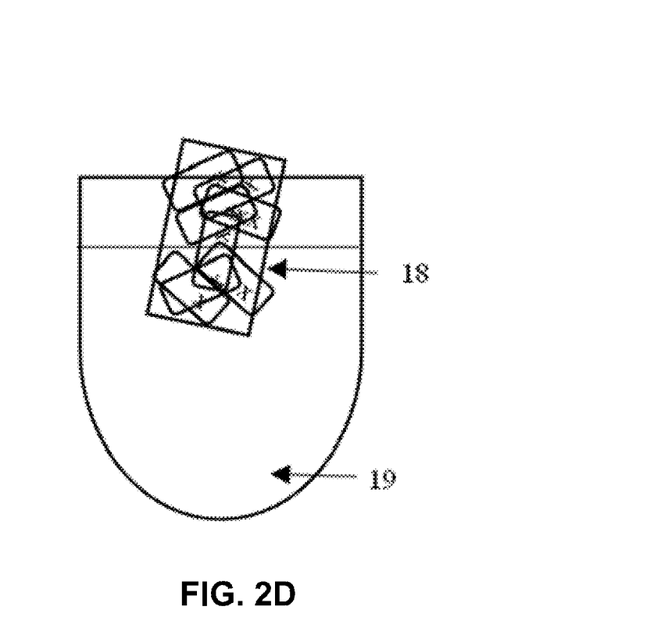
FIG. 2D illustrates a method for dyeing textiles according to the present invention showing a dyed substrate being removed from a culture medium.
Figure 2E:
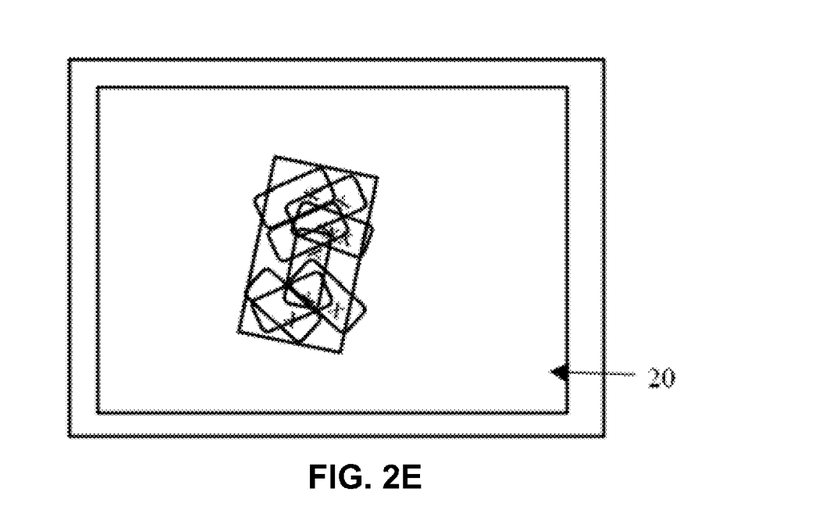
FIG. 2E illustrates a method for dyeing textiles according to the present invention showing a dyed substrate being subjected to a heat treatment.

In a second dyeing step, the dyed substrate (18) is removed from the culture medium and washed in a water bath (19) to remove residual carbon sources and microorganism detritus from the substrate. Waste wash water, which may contain residual quantities of free microorganisms, can be reused in subsequent dyeing batches or sterilized in a mild bleach or steam autoclave. The dyed substrate is subjected to a heat treatment step such dry ironing (not shown) or steam autoclaving (20) or microwave (not shown). In all cases the applied temperature should be higher than 100° C., preferably 121° C. This second dyeing step performs the dual role of (a) releasing the dye from microorganisms directly onto the substrates onto which the microorganisms have become adsorbed through lysation, and (b) fixing dye release with the lysate onto the substrate. Dye fixation and sterilization of waste wash water can be performed in the same autoclave cycle.

Figure 2F:
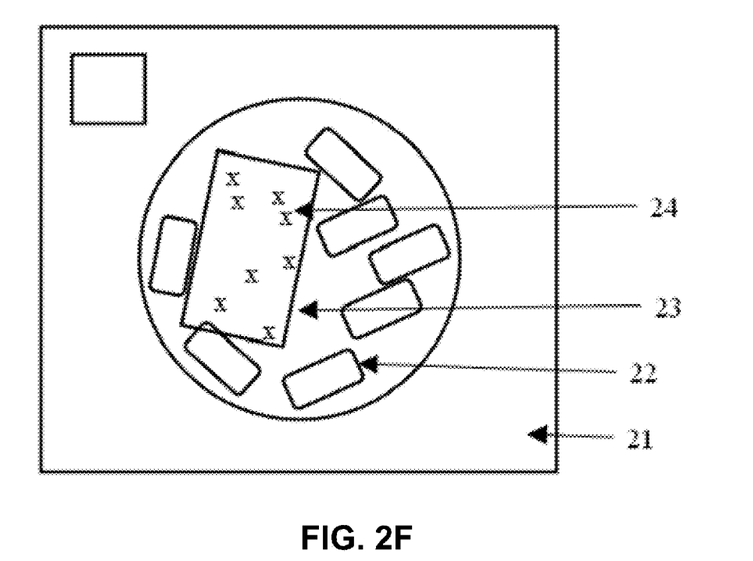
FIG. 2F illustrates a method for dyeing textiles according to the present invention showing a washing machine removing lysed microorganisms from a substrate having dye molecules fixed to its fibers.

A washing machine (21) operating using standard settings (for example 40° C. wash using bio detergent) removes lysed microorganisms (22) from the substrate (23) with dye molecules (24) fixed to its fibers. The washed substrate is dried using standard methods (not shown).

Figure 3:
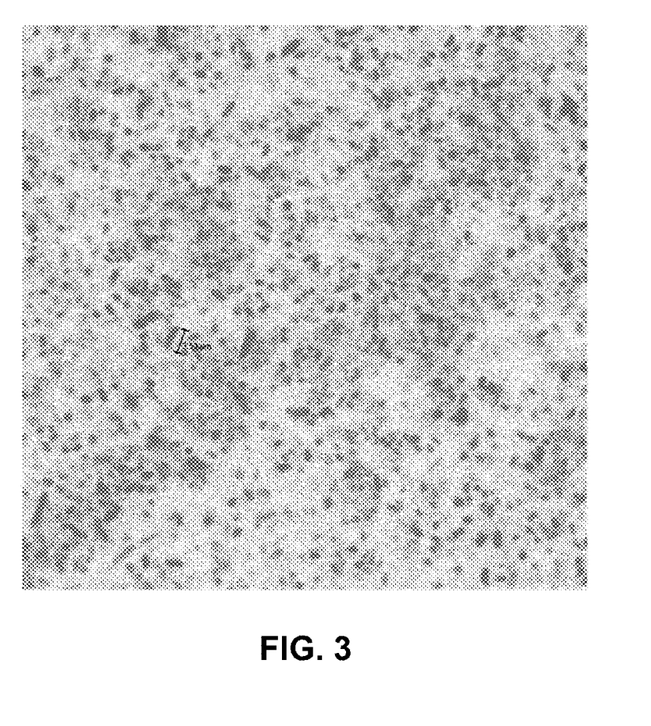
FIG. 3 is a micrograph showing *E. coli* grown in a liquid culture in a 1% (v/v) concentration of glycerol in 50% (v/v) LB medium and water.

FIG. 3 shows the growth of a microorganism in liquid culture, here *E. coli*, in a 1% (v/v) concentration of glycerol in 50% (v/v) LB medium and water. *E. coli* was grown for 24 hours in 50% (v/v) LB medium (10 g NaCl, 5 g Yeast Extract, 1 g Peptone, 1 L water) and 1% (v/v) glycerol. The microorganism has grown successfully and the measured average bacteria length is approximately 3.5 microns.

Figure 4:
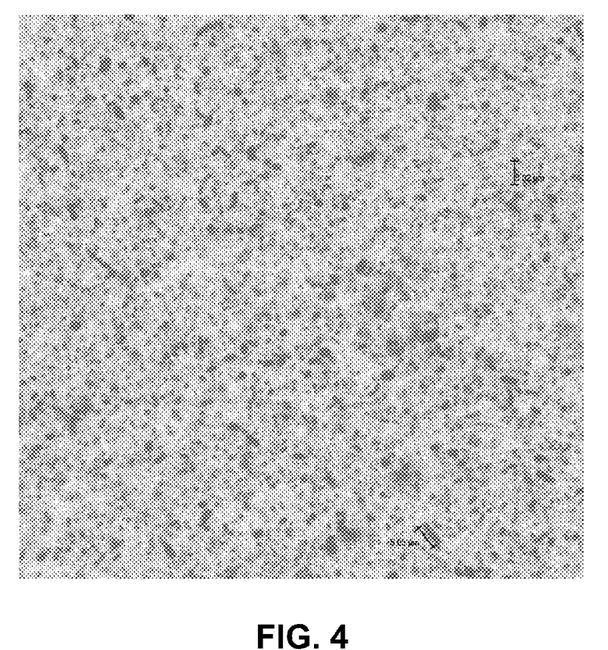
FIG. 4 is a micrograph showing *E. coli* grown in a liquid culture in a 5% (v/v) concentration of glycerol in 50% (v/v) LB medium and water.
Figure 5:
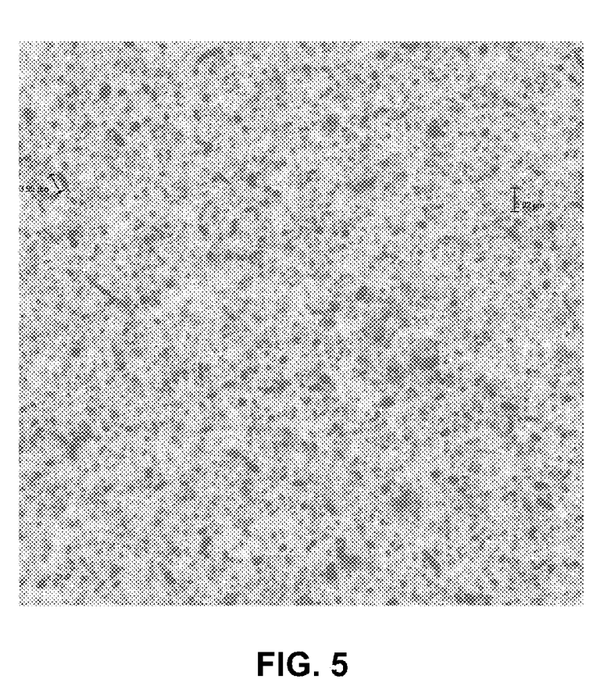
FIG. 5 is a micrograph showing *E. coli* grown in a liquid culture in a 5% (v/v) concentration of glycerol in 50% (v/v) LB medium and water.

FIG. 4 and FIG. 5 show the growth of a microorganism in liquid culture, here *E. coli*, in a 5% (v/v) concentration of glycerol in 50% (v/v) LB medium and water. *E. coli* was grown for 24 hours in 50% (v/v) LB medium (10 g NaCl, 5 g Yeast Extract, 1 g Peptone, 1 L water) and 5% (v/v) glycerol. The microorganisms have grown successfully though not as much as the 1% (v/v) concentration. The measured average bacteria length is in the range 4 microns to 5 microns.

Figure 6:
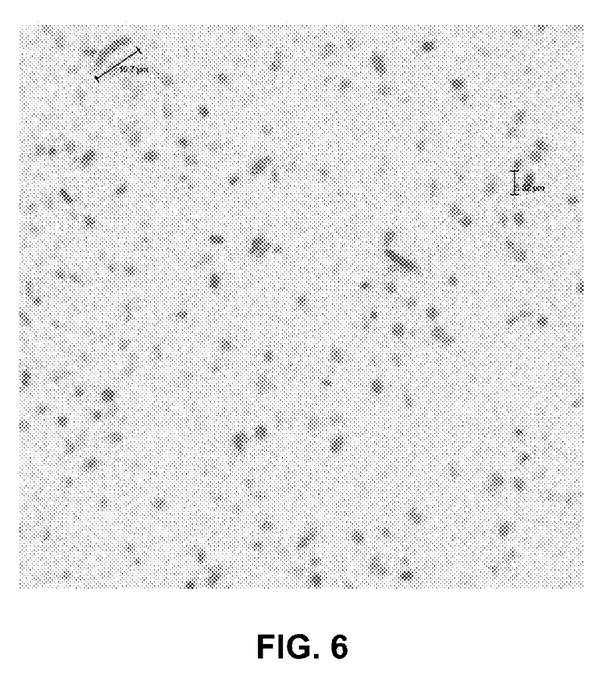
FIG. 6 is a micrograph showing *E. coli* grown in a liquid culture in a 10% (v/v) concentration of glycerol in 50% (v/v) LB medium and water.

FIG. 6 shows the growth of a microorganism in liquid culture, here *E. coli*, in a 10% (v/v) concentration of glycerol in 50% (v/v) LB medium and water. *E. coli* was grown for 24 hours in 50% (v/v) LB medium (10 g NaCl, 5 g Yeast Extract, 1 g Peptone, 1 L water) and 10% (v/v) glycerol. Microorganism growth is substantially lower than the 1% (v/v) case. The measured average microorganism length is 11 microns. Microorganisms have become curved along their length.

Figure 7:
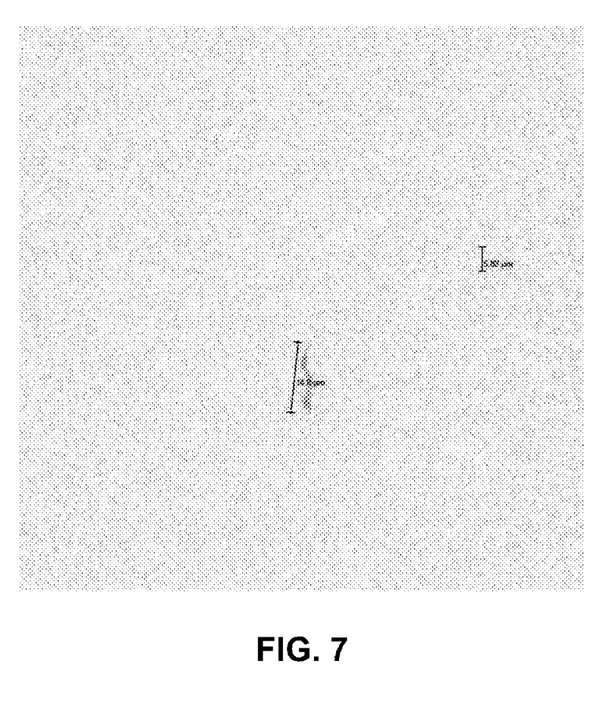
FIG. 7 is a micrograph showing *E. coli* grown in a liquid culture in a 20% (v/v) concentration of glycerol in 50% (v/v) LB medium and water.
Figure 8:
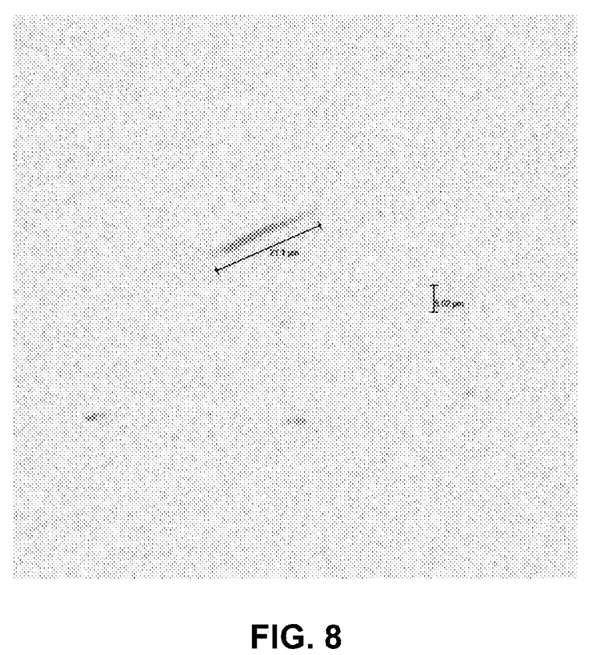
FIG. 8 is a micrograph showing *E. coli* grown in a liquid culture in a 20% (v/v) concentration of glycerol in 50% (v/v) LB medium and water.

FIG. 7 and FIG. 8 show the growth of a microorganism in liquid culture, here *E. coli*, in a 20% (v/v) concentration of glycerol in 50% (v/v) LB medium and water. *E. coli* was grown for 24 hours in 50% (v/v) LB medium (10 g NaCl, 5 g Yeast Extract, 1 g Peptone, 1 L water) and 20% (v/v) glycerol. Microorganism growth is very substantially lower than the 1% (v/v) case. The measured bacteria length is in the range 15 microns to 20 microns. Microorganisms have become substantially curved along their length.

Figure 9:
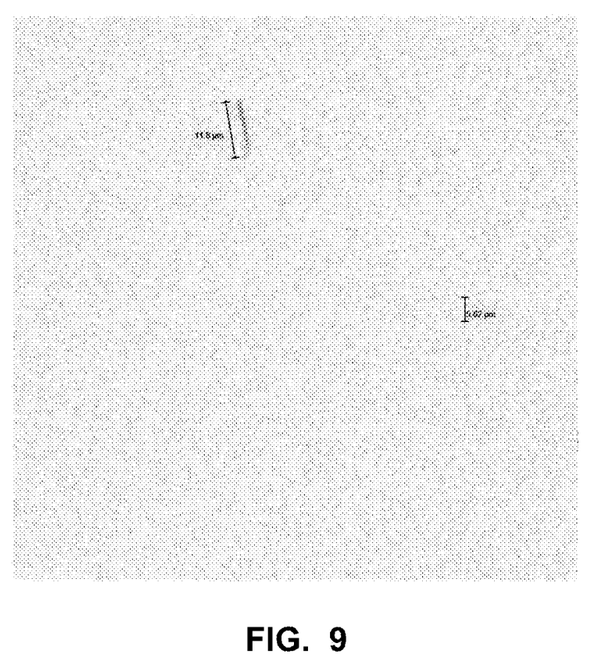
FIG. 9 is a micrograph showing *E. coli* grown in a liquid culture in a 50% (v/v) concentration of glycerol in 50% (v/v) LB medium and water.
Figure 10:
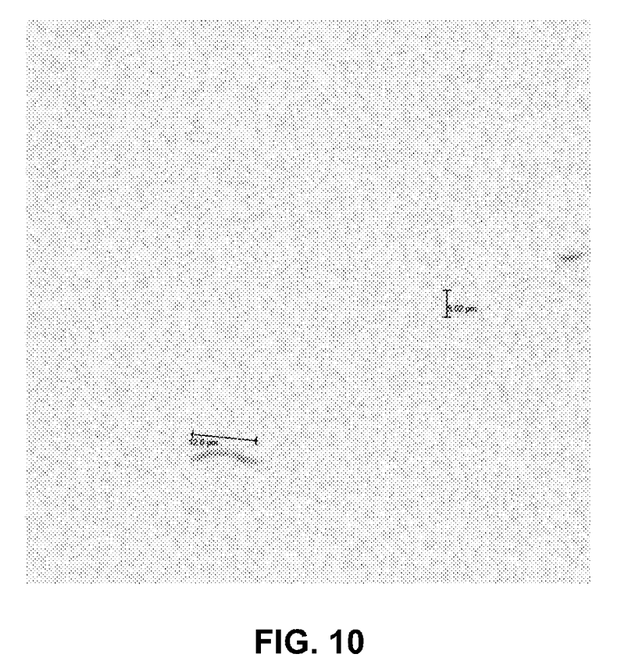
FIG. 10 is a micrograph showing *E. coli* grown in a liquid culture in a 50% (v/v) concentration of glycerol in 50% (v/v) LB medium and water.
Figure 11:
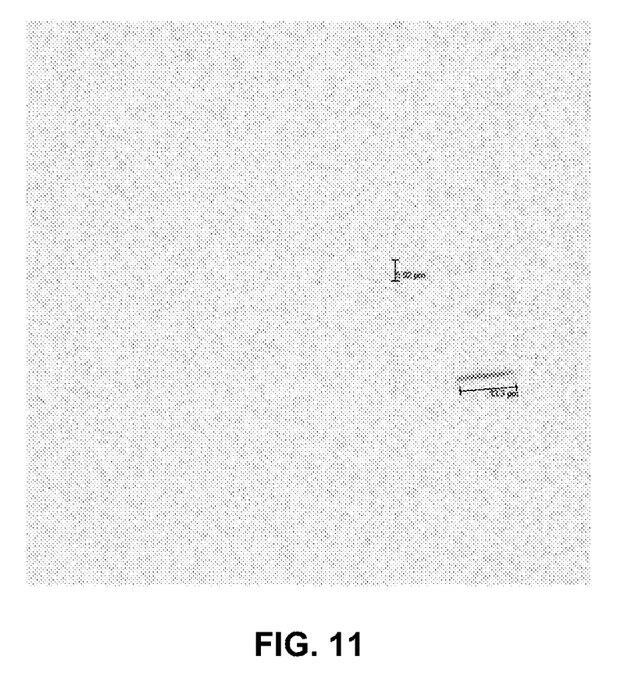
FIG. 11 is a micrograph showing *E. coli* grown in a liquid culture in a 50% (v/v) concentration of glycerol in 50% (v/v) LB medium and water.

FIG. 9 to FIG. 11 show the growth of a microorganism in liquid culture, here *E. coli*, in a 50% (v/v) concentration of glycerol in 50% (v/v) LB medium and water. *E. coli* was grown for 24 hours in 50% (v/v) LB medium (10 g NaCl, 5 g Yeast Extract, 1 g Peptone, 1 L water) and 50% (v/v) glycerol. Microorganism growth is very substantially lower than the 1% (v/v) case. The measured bacteria length is in the range 10 microns to 15 microns. Microorganisms have become substantially warped along their length.

Employable Media Additives:

Medium compositions involved the addition of salts examples of which include, but are not limited to: NaCl, KCl, CaCl2, MgCl2, MnCl2, ZnCl2, alone or in combination. Medium compositions involved the addition of an amino acid source, examples of which include, but are not limited to: Tryptone, Peptone, Bacto-peptone, Casein-amino acids, alone or in combination. Medium compositions involved the addition of a carbon source, examples of which include, but are not limited to: Yeast extract, Sucrose, Glucose, Glycerol, Fructose, Xylose, Lactose, Arabinose, alone or in combination. Medium compositions involved the addition of a nitrogen source, examples of which include, but are not limited to: yeast extract, Tryptone, Peptone, Bacto-peptone, Casein-amino acids, alone or in combination. All of the above medium additives may be employed with varying results, depending on the organism used for the pre-treatment process.

Growth Conditions:

Optimal growth conditions vary with the microorganism employed for the pre-treatment process. Parameters which greatly affect the end result include but are not limited to: pH, Salinity and Temperature.

As an example of the embodiment of this claim, a K12 derivative of *E. coli* which has been modified to produce high quantities of violacein was used to pre-treat the following substrates: silk, wool, rayon, polyester, elastaine and cotton. Varied growth conditions were tested, with pH ranges between 5-9, salinity ranges of 0.1% to 3%, and temperatures between 20° C. and 42° C. Optimum ranges for these parameters were found to be: pH 5.8-8.2, salinity 0.5%-1.5% and temperature: 30° C. to 40° C.

Pre-treatment facilitates the interaction between the dye-containing vessel (microorganism) and the substrate (fabric). To achieve this effect, the employed microorganism is grown in a suitable medium (see medium composition above) for a period of 12-48 hours depending on the inoculant-to-inoculate ratio, medium composition employed and growth conditions used. The entire culture is then supplemented with additional medium (see medium composition above) and the substrate is added at this point. Pre-treatment takes place within a similar time frame as the growth period.

Dye deposition is achieved via localized production and release of the dye by the microorganisms which have permeated the substrate. Increased local concentrations lead to higher dye uptake and the absence of large amounts of free dye in solution lead to a substantially reduced amount of waste product. Dye deposition rates will vary depending on which pigment is being produced as well as what microorganism is being employed.

These parameters will vary with the cytotoxicity of the pigment produced by the microorganism, the water solubility of the pigment, the pigment affinity for the substrate and the growth conditions employed (see growth conditions above). As an example of embodiment of this claim, a K12 derivative of *E. coli* which has been modified to produce high quantities of violacein was used to deposit dyes on/in the following substrates: silk, wool, rayon, polyester, elastaine, cotton and flax. Nearly complete penetration and association of the violacein-producing/containing *E. coli* with the substrate was observed within two hours post substrate addition to the supplemented medium and continues throughout the substrate incubation period.

Finishing Step:

A final finishing step is achieved via exposure of the treated substrate to temperatures exceeding 121° C. This has the dual purpose of inactivating all microorganisms present on the substrate as well as fixation of the dye to the substrate.

The vast majority of dye present in the inactivated microorganism is transferred to the substrate due to lysis. The finishing step then involves a final wash, which removes the vast majority of inactivated microorganisms and microorganism related compounds from the substrate. The final substrate has then been sterilized and cleaned to a standard nearing medical device requirements.

Waste Products:

Unincorporated dye (dye waste) is below the industry standard of 3% and a level of incorporation has been achieved by the invented process that surpasses 99.997% efficiency. Spent medium such as the dissolved salts, amino acids and carbon sources, remaining after the dyeing process can be recycled and re-used for subsequent dyeing processes using either the same or a different microbiological dye. Thus via at least two routes—firstly less water use during the initial dyeing process and secondly the ability to re-use spent media solutions without treatment—water use is reduced in the described methods when compared to conventional methods.

What is claimed is:

1. A method for applying a microbiologically-produced factor to a substrate, comprising:
   a. culturing a factor-producing microorganism in the presence of a substrate to which the microbiologically-produced factor is to be applied, and in the presence of a growth medium comprising a carbon source at a concentration of 10% (v/v) to 90% (v/v), such that the microorganism is cultured in contact with the substrate and the growth of the microorganism is substantially lower than when the carbon source is present at a concentration of 1% (v/v), to cause the microorganism to adsorb to the substrate;
   b. removing the substrate from the growth medium:
   c. lysing the cultured microorganism to release microbiologically-produced factor in contact with the substrate; and
   d. fixing the released microbiologically-produced factor onto the substrate.

2. The method of claim 1, wherein the concentration of the carbon source depends on the carbon source selected to optimize the transfer rate of factor-containing microorganisms to the substrate, and the quality of subsequent microbiologically-produced factor fixation to the substrate.

3. The method of claim 1, wherein the lysing and the fixing are carried out in a single process.

4. The method of claim 1, wherein the lysing and fixing are carried out by exposing the substrate and microorganisms to heat above 101° C.

5. The method of claim 1, further comprising initially culturing the factor-producing microorganism in the absence of the substrate to which the microbiologically-produced factor is to be applied, prior to step 1a.

6. The method of claim 1, further comprising washing the substrate to which the microbiologically-produced factor has been applied to remove waste contaminants prior to and post step 1c.

7. The method of claim 1, wherein two or more different factor-producing microorganism species are used simultaneously.

8. The method of claim 1, wherein two or more different microbiologically-produced factors are produced by one or more different microorganisms.

9. The method of claim 1, wherein the substrate is selected from the group consisting of natural, synthetic, semi-synthetic and mixed substrates.

10. The method of claim 9, wherein the substrate comprises a member selected from the group consisting of silk, cotton, flax, wool, and leather.

11. The method of claim 9, wherein the substrate comprises a member selected from the group consisting of rayon and acetate.

12. The method of claim 9, wherein the substrate comprises a member selected from the group consisting of polyester, nylon, acrylic, elastane, polyvinyl and petrochemical derivatives.

13. The method of claim 1, wherein the microorganism is a eukaryotic organism.

14. The method of claim 13, wherein the eukaryotic organism is selected from the group consisting of plant, algae, fungi, worms and arthropods.

15. The method of claim 1, wherein the microorganism is a prokaryotic organism.

16. The method of claim 15, wherein the prokaryotic organism is selected from the group consisting of archae and eubacteria.

17. The method of claim 15, wherein the prokaryotic organism is a Gram positive bacteria selected from the group consisting of *Bacillus* spp. and *Clostridium* spp.

18. The method of claim 15, wherein the prokaryotic organism is a Gram negative bacteria selected from the group consisting of *Eschericia* spp *Pseudomonas* spp., *Chromobacterium* spp., and *Janthinobacter* spp.

19. The method of claim 1, wherein the microorganism is genetically modified.

20. The method of claim 1, wherein the culturing takes place in a growth environment selected from the group consisting of incubators, shaking incubators, fermenters and biofermenters.

21. The method of claim 1, wherein the culturing takes place at a temperature of 1° C. to 150° C.

22. The method of claim 1, wherein the culturing takes place at a carbon dioxide concentration of 0% to 10%.

23. The method of claim 1, wherein the culturing takes place at a pH of 1.5 to 9.5.

24. The method of claim 1, wherein the growth medium is selected from the group consisting of a first broth comprising NaCl, yeast extract and peptone, a second broth comprising yeast extract, tryptone, glycerol and phosphate buffer, a third broth comprising tryptone, yeast extract, NaCl, KCl, $MgCl_2$ and $MgSO_4$, a fourth broth comprising tryptone, yeast extract, NaCl, KCl, $MgCl_2$, $MgSO_4$ and glucose, and a fifth broth comprising yeast extract, peptone and glucose or dextrose.

25. The method of claim 1, wherein the carbon source is selected from the group consisting of dextrose, glucose, sucrose, potato starch, citrate, lactose, maltose, glycerol, xanthose, and arabinose.

26. The method of claim 1, wherein the carbon source is present at a concentration of 15% (v/v) to 60% (v/v).

27. The method of claim 1, wherein the carbon source is present at a concentration of 20% (v/v) to 40% (v/v).

28. A method for applying a microbiologically-produced factor to a substrate, comprising:
- a. culturing a factor-producing microorganism in the presence of a substrate to which the microbiologically-produced factor is to be applied, and in the presence of a growth medium comprising a carbon source at a concentration of 10% (v/v) to 90% (v/v), such that the microorganism is cultured in contact with the substrate and the growth of the microorganism is substantially lower than when the carbon source is present at a concentration of 1% (v/v), to cause the microorganism to adsorb to the substrate;
- b. lysing the cultured microorganism to release microbiologically-produced factor in contact with the substrate; and
- c. fixing the released microbiologically-produced factor onto the substrate;

wherein the microorganism is selected from the group consisting of eukaryotic microorganisms and bacteria, and the carbon source is selected from the group consisting of sucrose, glucose, glycerol, fructose, xylose, lactose, arabinose, maltose, xanthoses, citrate, potato starch, yeast extract and mixtures thereof.

29. The method of claim 28, wherein the substrate is selected from the group consisting of cotton, elastane, nylon, polyester, silk, rayon, wool, and mixed substrates.

30. The method of claim 28, wherein the carbon source is present at a concentration of 20% (v/v) to 50% (v/v).

* * * * *

UNITED STATES PATENT AND TRADEMARK OFFICE
CERTIFICATE OF CORRECTION

PATENT NO. : 11,105,041 B2
APPLICATION NO. : 16/692390
DATED : August 31, 2021
INVENTOR(S) : Nugent et al.

Page 1 of 1

It is certified that error appears in the above-identified patent and that said Letters Patent is hereby corrected as shown below:

On the Title Page

Item [30] Foreign Application Priority Data:
Please delete "1506018" and insert --1506018.9--

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*